(12) United States Patent
Hacker et al.

(10) Patent No.: US 11,103,700 B2
(45) Date of Patent: Aug. 31, 2021

(54) STIMULATION PROBE FOR ROBOTIC AND LAPAROSCOPIC SURGERY

(71) Applicant: Medtronic Xomed, Inc., Jacksonville, FL (US)

(72) Inventors: David C. Hacker, Jacksonville, FL (US); Wenjeng Li, Saint Johns, FL (US); Kevin Lee McFarlin, Saint Johns, FL (US)

(73) Assignee: Medtronic, Inc., Minneapolis, MN (US)

( * ) Notice: Subject to any disclaimer, the term of this patent is extended or adjusted under 35 U.S.C. 154(b) by 412 days.

(21) Appl. No.: 15/646,199

(22) Filed: Jul. 11, 2017

(65) Prior Publication Data

US 2017/0304617 A1    Oct. 26, 2017

Related U.S. Application Data

(62) Division of application No. 13/455,760, filed on Apr. 25, 2012.

(51) Int. Cl.
| | |
|---|---|
| *A61N 1/36* | (2006.01) |
| *A61B 5/00* | (2006.01) |
| *A61B 5/377* | (2021.01) |
| *A61B 34/30* | (2016.01) |

(52) U.S. Cl.
CPC .......... *A61N 1/36017* (2013.01); *A61B 5/377* (2021.01); *A61B 5/4893* (2013.01); *A61B 34/30* (2016.02)

(58) Field of Classification Search
CPC . A61B 19/2203; A61B 5/0484; A61B 5/4893; A61N 1/36017
See application file for complete search history.

(56) References Cited

U.S. PATENT DOCUMENTS

| | | | | |
|---|---|---|---|---|
| 5,190,561 | A | * | 3/1993 | Graber ............. A61B 17/00234 606/114 |
| 6,139,545 | A | * | 10/2000 | Utley ..................... A61B 5/053 606/34 |
| 6,165,180 | A | | 12/2000 | Cigaina et al. |
| 6,292,701 | B1 | | 9/2001 | Prass et al. |
| 6,298,256 | B1 | | 10/2001 | Meyer |
| 6,451,027 | B1 | * | 9/2002 | Cooper ............. A61B 1/00149 606/130 |
| 6,477,423 | B1 | | 11/2002 | Jenkins |

(Continued)

FOREIGN PATENT DOCUMENTS

| | | |
|---|---|---|
| CN | 101594830 A | 12/2009 |
| CN | 102525383 A | 7/2012 |

(Continued)

OTHER PUBLICATIONS

PCT Search Report and Written Opinion, PCT/US2013/038011, dated May 26, 2014, 16 pages.

(Continued)

*Primary Examiner* — Patrick Fernandes
(74) *Attorney, Agent, or Firm* — Dicke, Billig & Czaja, PLLC

(57) ABSTRACT

A stimulation probe includes a proximal end connector and a flexible wire coupled to the end connector. A handle is coupled to the wire and a needle extends from the handle and terminates at a conductive tip.

6 Claims, 3 Drawing Sheets

(56) References Cited

U.S. PATENT DOCUMENTS

| | | |
|---|---|---|
| 7,987,001 B2 | 7/2011 | Teichman et al. |
| 8,137,285 B1 | 3/2012 | Regan et al. |
| 8,715,223 B2 | 5/2014 | McKay |
| 2001/0010010 A1* | 7/2001 | Richmond ............ A61N 1/3601 607/42 |
| 2004/0193146 A1 | 9/2004 | Lee |
| 2005/0283148 A1 | 12/2005 | Janssen et al. |
| 2006/0025702 A1 | 2/2006 | Sterrantino et al. |
| 2007/0021803 A1 | 1/2007 | Deem et al. |
| 2008/0183189 A1 | 7/2008 | Teichman et al. |
| 2008/0281313 A1* | 11/2008 | Fagin ................ A61B 5/04001 606/34 |
| 2009/0069803 A1* | 3/2009 | Starkebaum ......... A61N 1/0509 606/41 |
| 2009/0149867 A1* | 6/2009 | Glozman ........... A61B 17/3478 606/130 |
| 2009/0210041 A1 | 8/2009 | Kim et al. |
| 2010/0076534 A1* | 3/2010 | Mock ................... A61N 1/0502 607/116 |
| 2011/0022028 A1 | 1/2011 | Mckay |
| 2011/0270120 A1 | 11/2011 | McFarlin et al. |
| 2012/0086791 A1 | 4/2012 | Zheng et al. |
| 2012/0123292 A1 | 5/2012 | Fagin et al. |

FOREIGN PATENT DOCUMENTS

| | | | |
|---|---|---|---|
| CN | 202776532 U | 3/2013 | |
| CN | 102470243 A | 5/2014 | |
| DE | 3919453 A1 * | 12/1989 | ........... A61N 1/0512 |
| WO | 2006029257 A2 | 3/2006 | |
| WO | 2009124726 A1 | 10/2009 | |
| WO | 2011136962 A1 | 11/2011 | |

OTHER PUBLICATIONS

Medtronic ENT, "Intraoperative Nerve Monitoring Accessories", Monitoring Accessories for NIM Nerve Integrity Monitors, Copyright 2009, 8 pages.

Ntuitive Surgical, Inc., "EndoWrist", Instrument & Accessory Catalog, Aug. 2008, 21 pages.

Final Office Action, U.S. Appl. No. 13/455,760, dated Jul. 6, 2020, 20 pages.

* cited by examiner

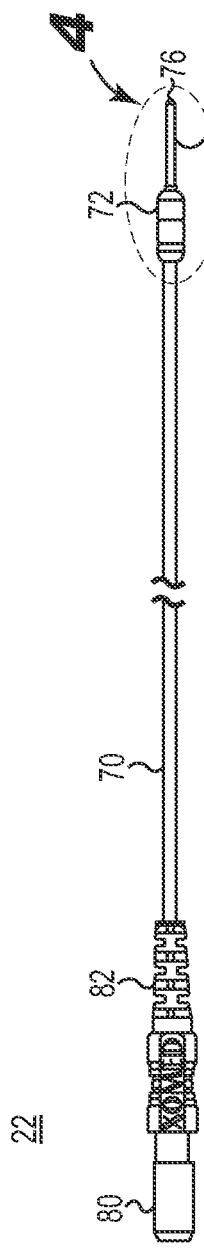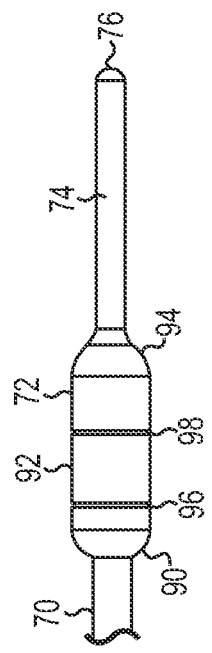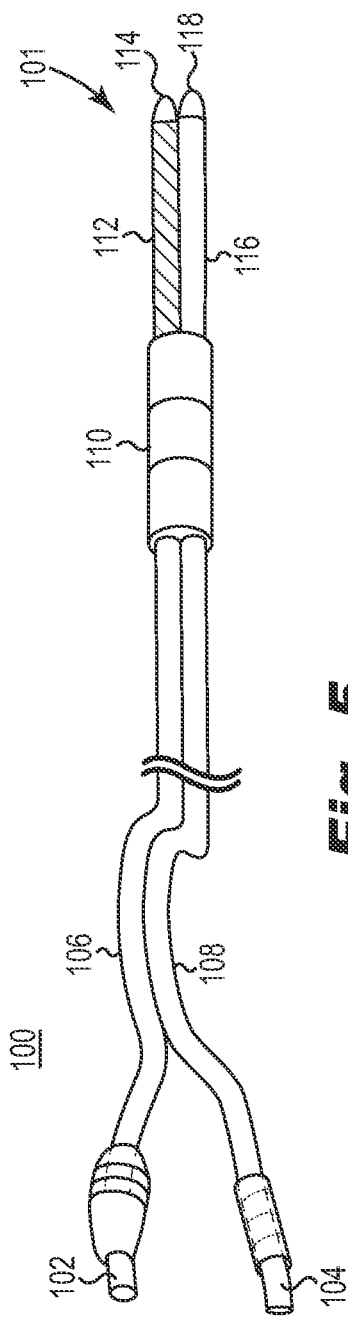

STIMULATION PROBE FOR ROBOTIC AND LAPAROSCOPIC SURGERY

CROSS-REFERENCE TO RELATED APPLICATION

This application is a divisional of U.S. patent application Ser. No. 13/455,760 filed Apr. 25, 2012, the disclosure of the above-identified application is hereby incorporated by reference in its entirety.

BACKGROUND

Evoked potential (EP) monitoring assists a surgeon in locating nerves within an obscured surgical field, as well as preserving and assessing nerve function in real-time during surgery. To this end, evoked potential monitoring is commonly employed to capture responses resulting from stimulation of the tissue of interest (e.g., direct nerve, muscle, etc.). Evaluating the aforementioned EP responses allows for immediate assessment of the integrity of the electrical signal path through the tissue of interest. Electrical stimulation can cause excitement of the tissue. During electrical stimulation, a surgical probe applies a stimulus signal near the area where the subject tissue may be located. If the stimulation probe contacts or is reasonably near the tissue, the applied stimulus signal is transmitted to the tissue evoking a response. Excitation of the tissue generates an electrical impulse that is sensed by the recording electrodes (or other sensing device). The recording electrode(s) signal the sensed electrical impulse information to the surgeon for interpretation in the context of determining (EP) activity. For example, the EP activity can be displayed on a monitor and/or presented audibly.

Evoked potential monitoring is useful for a multitude of different surgical procedures or evaluations that involve or relate to nerve conduction. Evaluation of these nerves can assist in preservation of the intended electrophysical function during procedures where there exists a high probability of damage to these tissues. For example, various head and neck surgical procedures (e.g., parotidectomy and thyroidectomy) require locating and identifying cranial and peripheral motor nerves. In some instances, it is desirable to utilize a surgical robot to assist the surgeon in performing a surgical procedure. Surgical robots can perform procedures laparoscopically in a manner that is minimally invasive to the patient. Due to various constraints involved in a minimally invasive setting, conventional stimulating probes are not equipped to be used in such an environment.

SUMMARY

A stimulation probe includes a proximal end connector and a flexible wire coupled to the end connector. A handle is coupled to the wire and a needle extends from the handle and terminates at a conductive tip.

BRIEF DESCRIPTION OF THE DRAWINGS

FIG. 3 is a side view of the stimulation probe shown in FIG. 2.

FIG. 4 is a close-up side view of a distal end of the stimulation probe as indicated by ellipse 4 in FIG. 3.

FIG. 5 is a side view of an alternative stimulation probe, including a distal bipolar stimulation assembly.

DETAILED DESCRIPTION

Figure 1:
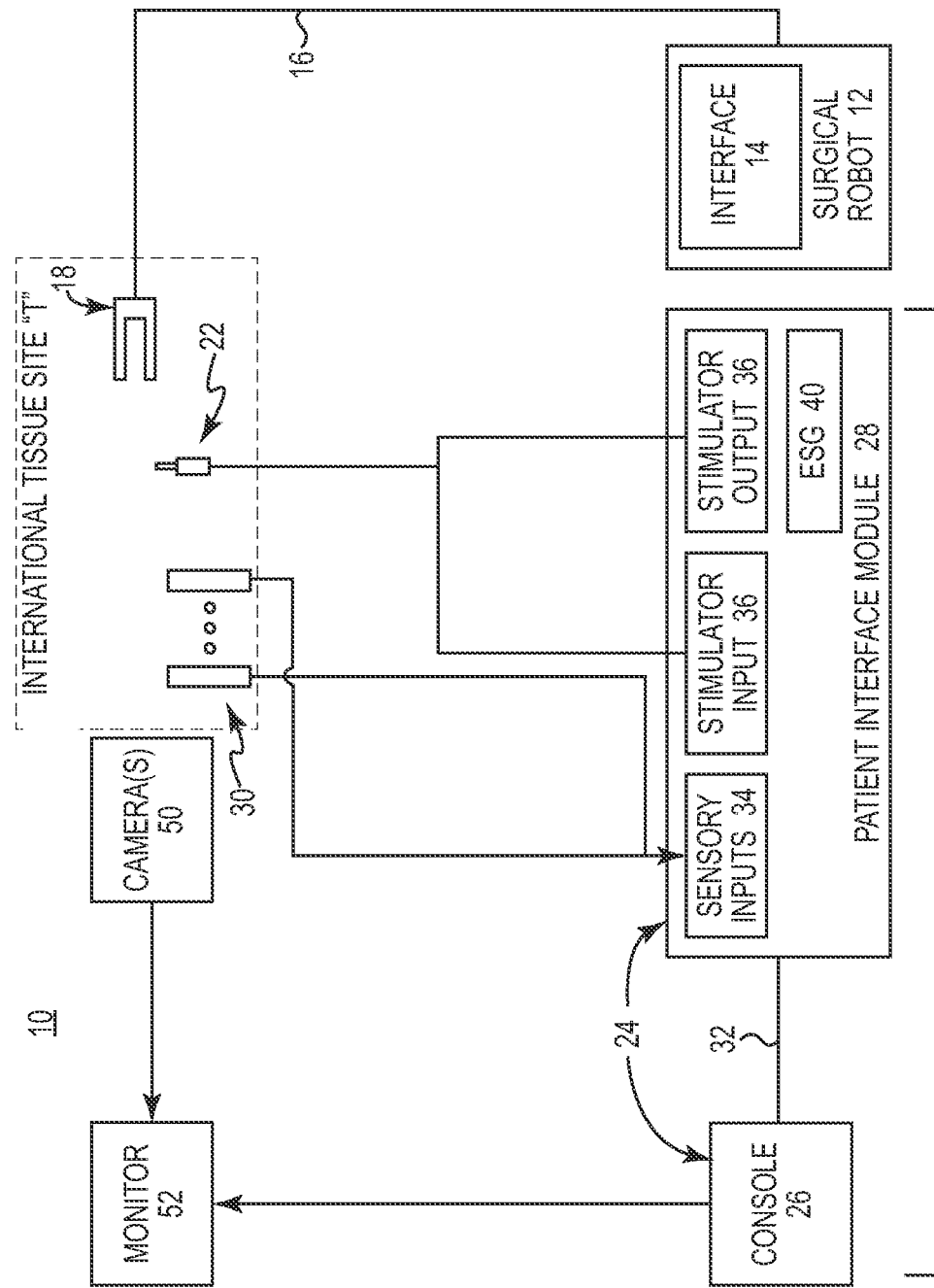
FIG. 1 is a schematic block diagram of a robotic surgical system.

FIG. 1 is a schematic block diagram of a robotic surgical system 10 utilizing specific implementations of components to selectively perform nerve monitoring at an internal target tissue site "T". In one embodiment, the internal target tissue site "T" is accessed laparoscopically and surgery is performed using a surgical robot 12 such as a DaVinci surgical system robot available from Intuitive Surgical, Inc. of Sunnyvale, Calif. The robot 12 includes an interface 14 for selective control by a user (e.g., a surgeon) and at least one arm 16 terminating at an instrument 18. Instrument 18 is a wristed instrument forming a grasper, a forceps, a holder or similar structure coupled to the arm 16 and capable of control by the robot 12. To this end, instrument 18 includes a jaw formed of opposed arms that are capable of movement relative to one another.

An evoked potential (EP) monitoring system 20 is coupled to a stimulating probe 22 so as to deliver stimulation signals to the tissue site "T" in order to locate nerves. In general terms, the evoked potential monitoring system 20 is configured to assist in and perform nerve integrity monitoring for virtually any nerve/muscle combination of the human anatomy, as well as recording nerve potential. The system 20 includes a control unit 24, which can assume a wide variety of forms and in one embodiment includes a console 26 and a patient interface module 28.

System 20 further includes one or more sensing probes 30, which can be any type of sensing device such as an electrode and can operate to complete a circuit that includes the probe 22. In a laparoscopic surgical environment, sensing probes 30 can be coupled to tissue internal to a patient through a suitable introducer such as a cannula, trocar, etc. The control unit 24 facilitates stimulation of the instrument 10, as well as processes all information generated by probe 22, sensing probes 30 and other components (not shown) during use. The probe 22 and the control unit 24 are adapted to allow control and variation of a stimulus energy delivered to, and thus a stimulus level delivered by, the probe 22. Further, the control unit 24 processes information (e.g., patient response) received from stimulation probe 22 and/or sensing probes 30 resulting from delivered stimulation.

Using the sensing probes 30, the system 20 performs monitoring based upon recorded EP activity in response to an electrical current energy delivered by the stimulation probe 22 and/or physical manipulation of tissue. With the one embodiment of FIG. 1, the console 26 and the patient interface module 28 are provided as separate components, communicatively coupled by a cable 32. Alternatively, a wireless link can be employed. Further, the console 26 and the patient interface module 28 can be provided as a single device. In basic terms, however, the patient interface module 28 serves to promote easy connection of stimulus/sensory components (such as the probe 22 and sensing probes 30), as well as to manage incoming and outgoing electrical signals. The console 26, in turn, interprets incoming signals (e.g., impulses sensed by sensing probes 30), displays information desired by a user, provides audible feedback of signals, presents a user interface (such as by including, for example, a touch screen), and delivers a stimulation energy to the probe 22 pursuant to control signals from the control unit 24 (via connection to the patient interface module 28, as well as other tasks as desired.

As previously described, the patient interface module 28 communicates with the console 26 through the cable 32 information to and from the stimulation probe 22, as well as information from the sensing probes 30. In effect, the patient interface module 28 serves to connect the patient (e.g., at tissue site "T") to the console 26. To this end, and in one embodiment, the patient interface module 28 includes one or more (preferably eight) sensory inputs 34, such as pairs of electrode inputs electrically coupled to receive signals from the sensing probes 30 (referenced generally in FIG. 1). In addition, the patient interface module 28 provides a stimulator input port 36 (referenced generally in FIG. 1) and a stimulator output port 38 (referenced generally in FIG. 1). The stimulator input port 36 receives control signals from the probe 22 relating to desired stimulation levels and/or other activities, whereas the stimulator output port 38 facilitates delivery of stimulation energy from an electrical stimulation generator 40 to the probe 22. The patient interface module 28 can further provide additional component port(s), such as a ground (or return electrode) jack, auxiliary ports for additional stimulator probe assemblies, etc.

The sensing probes 30 are coupled to the patient (e.g., selected tissue) to provide signals to the patient interface module 28. In one embodiment, the plurality of probes 30 includes eight probes that are electronically coupled to sensory inputs 34. In normal operation, the probes 30 sense electrical signals from the patient and send the signals to patient interface module 28. These signals include an electrical impulse from patient tissue, which is indicative of EP activity (e.g., a bio-electric response) in the patient. Upon sensing that probe 22 is proximate and/or contacting a nerve so as to create EP activity (e.g., as a result of signals from ESG 40), sensing probes 30 can provide a corresponding indication. As a result, damage to nerves in tissue site "T" can be prevented by providing an indication of the area contacting probe 22 should not be altered. In a further embodiment, control unit 24 can further provide an alert (e.g., an audible and/or visual signal) that sensing probes 30 are sensing EP activity.

In a further embodiment, one or more cameras 50 are positioned so as to provide visual information of the surgical site to assist the surgeon in performing the desired surgical procedure. The one or more cameras 50 can also be introduced to site "T" laparoscopically. Video data from the one or more cameras 50 can be provided to a monitor 52, along with data from console 26. To this end, the surgeon is provided with both visual information of the surgical site as well as visual information indicative of recorded responses from sensing probes 30 and/or probe 22. By selectively providing stimulation signals and RF signals, the surgeon, through use of monitor 52, can visually check whether a targeted site is a nerve or whether the targeted tissue can be cut. As such, a surgeon can quickly discern and cut targeted tissue.

Within the environment of FIG. 1, instrument 18 and stimulation probe 22 are both equipped to be introduced laparoscopically into tissue site "T" such that instrument 18 can grasp and manipulate probe 22 so as to stimulate selected tissue within tissue site "T". To this end, as discussed in detail below, probe 22 includes a flexible wire, conductive tip and handle configured to be grasped by instrument 18.

Figure 2:
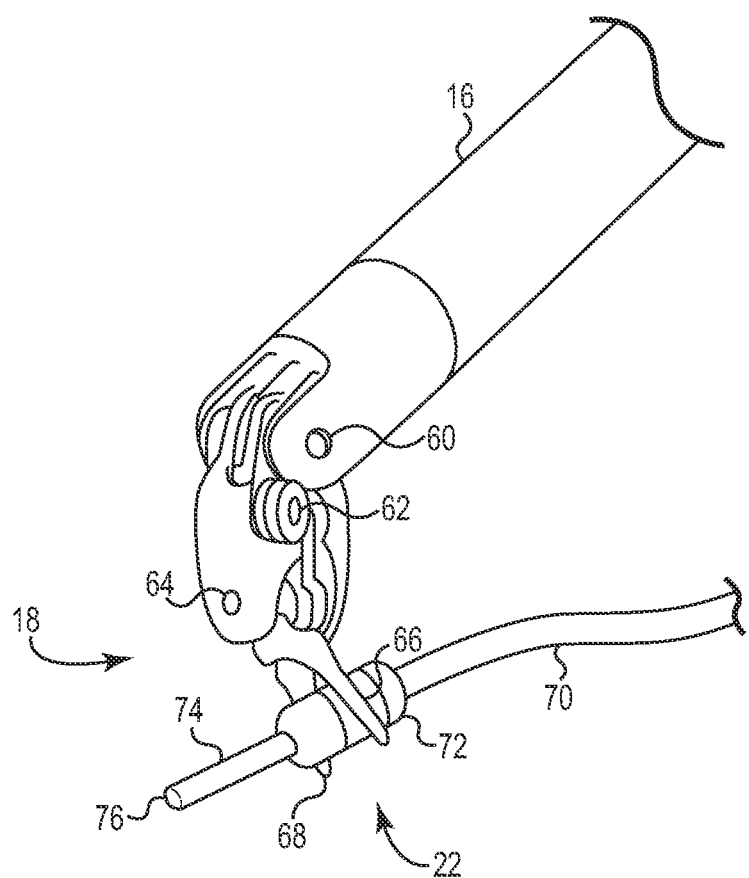
FIG. 2 is a perspective view of a surgical robotic arm grasping an exemplary stimulation probe.

FIG. 2 is a perspective view of arm 16 and instrument 18 grasping probe 22 within an internal surgical site. Instrument 18 is coupled to arm 16 through a swivel connection 60 that allows a range of movement of instrument 18 with respect to arm 16. Other swivel connections 62 and 64 are further provided to impart additional functionalities and/or ranges of motion for instrument 18. Instrument 18 terminates in a pair of opposed jaw 66 and 68 that are moveable relative to one another through swivel connection 64. Probe 22 includes features to allow instrument 18 to easily grasp the probe 22 and deliver the probe to a desired site for stimulation of the site. In particular, probe 22 includes a flexible wire 70, a handle 72 sized to be grasped by the jaws 66, 68 and an elongated needle or shaft 74 terminating at a conductive tip 76.

FIG. 3 is a side view of the probe 22, extending from the conductive tip 76 positioned at a distal end of the probe 22 to a proximal end 80. Adjacent to the proximal end 80 is a flexible strain relief member 82 coupled to the wire 70. End 80 forms a conductive connector configured to connect with patient interface module 28 (FIG. 1) and/or otherwise coupled to an interface that will provide signals to stimulator input 36 and/or receive signals from stimulator output 38. End 80 is electrically coupled with the wire 70, which is further electrically coupled to the conductive tip 76. In one embodiment, flexible wire 70 is sufficiently long to extend from the patient interface module 28 to the tissue site "T". To this end, in one embodiment, wire 70 is approximately 2 meters in length. During use, the needle 74 and handle 72 are introduced completely into the tissue site "T", the flexibility of the wire 70 being such that instrument 18 can easily grasp and move the conductive tip 76 to a desired region for EP monitoring. To this end, a portion of the wire 70 is positioned within the patient at tissue site "T", whereas a portion, including end 80 and strain relief member 82, is positioned outside the patient.

FIG. 4 is a detailed view of the distal end of probe 22. As illustrated, handle 72 includes a curved proximal end 90 coupled to wire 70, an elongated grasping portion 92 and a curved distal end 94 coupled to needle 74. Grasping portion 92 further includes a first groove 96 and a second groove 98, which can provide additional features for which instrument 18 can grasp. Handle 72 and needle 74, in one embodiment, are sized for laparoscopic use. For example, a length of the handle 72 and needle 74 (as measured from proximal end 90 to distal tip 76), in one embodiment, is less than 3.0 centimeters (cm) and in further embodiments is less than 2.5 cm and less than 2.0 cm. To this end, handle 72 and needle 74 can be introduced laparoscopically into a targeted laparoscopic surgical site and be configured for placement at a desired region of tissue. Additionally, desired ratios for dimensions of the handle 72 and needle 74 can be selected as desired. In one example, a ratio of handle diameter to needle diameter is approximately 3:1. In a further embodiment, a ratio of a length of needle 74 to a length of handle 72 is greater than 1:1 and in one embodiment is approximately 1.13521:1.

In one embodiment, a length of handle 72, as measured from proximal end 90 to distal end 94, is in an approximate range from 6-11 millimeters (mm) and in one particular embodiment is approximately 8.81 mm. Moreover, handle 72 is cylindrically shaped, having a diameter in an approximate range from 2-4 mm and in one particular embodiment is about 3.00 mm.

Needle 74 is electrically conductive and covered with an insulating sheath such that signals provided to the probe 22 are directly provided to the conductive tip 76. In one embodiment, conductive tip 76 can be characterized by an absence of insulating material, such that signals can be carried between end 80 and conductive tip 76. Needle 74, in one embodiment, has a length, as measured from connection to distal end 94 to an end of the conductive tip 76, in an approximate range of 7-13 mm and in one particular embodiment is approximately 10.00 mm. Furthermore, needle 74 is cylindrically shaped, having a diameter in an approximate range from 0.5-1.5 mm and in one particular embodiment about 1.00 mm. In yet a further embodiment, needle 74 is formed of stainless steel, such as 300 series or 400 series. To this end, a malleability characteristic of needle 74 can be adjusted such that arm 16 (FIG. 2) is capable of bending the needle 74 to various angles. Due to the malleability of needle 74, the needle 74 can be bent to various angles and/or shapes as desired. For example, while arm 16 holds handle 72, a second arm (not shown) similar in construction to arm 16 can grasp needle 74 so as to bend the needle 74 to a desired shape.

During use and with further reference to FIG. 2, instrument 18, and in particular jaws 66 and 68, grasp handle 72 so as to position the tip 76 in contact with tissue. The tip 76 can be rounded (e.g., forming a hemispherical surface) to prevent injury to tissue yet still allow stimulation to be precisely delivered.

Needle 74 can take various forms so as to provide several functions, as desired. For example, needle 74 can be shaped so as to provide dissection of a surgical site in addition to nerve monitoring. To that end, needle 74 can include a dissection tip such as a curved needle, elevator tip, ring dissector, sickle knife, duckbill elevator (i.e., wide and rounded terminal end), raspatory tip and/or combinations thereof.

In addition to taking various shapes, needle 74 can be a monopolar or a bipolar configuration. FIG. 5 illustrates an alternative probe 100 that includes a bipolar probe assembly 101 at a distal end of the probe 100. In contrast to probe 22, bipolar probe 100 defines multiple proximate connectors 102 and 104 electrically coupled to flexible wires 106 and 108, respectively. Probe 100 further includes a handle portion 110 constructed similar to handle 72 of probe 22 in both size and shape as discussed above. Moreover, probe 100 includes a first needle 112 terminating at a first conductive tip 114 and a second needle 116 terminating at a second conductive tip 118. In one embodiment, the first conductive tip 114 serves as a stimulating probe (i.e., a cathode), delivering stimulation signals from connector 102, along wire 106 and to tissue, whereas the second conductive tip 118 serves as a return probe (i.e., an anode) for signals delivered by the first conductive tip 114, along wire 108 to connector 104. In any event, components of probe 100 can be similar to and include similar features to components of probe 22. In a further embodiment, probe 100 can be a so-called concentric bipolar stimulator probe, wherein the cathode and anode share a common shaft and the conductive tip forms a spaced apart cathode and anode that deliver stimulation and sense any stimulation received, respectively.

Although the present disclosure has been described with reference to preferred embodiments, workers skilled in the art will recognize that changes can be made in form and detail without departing from the spirit and scope of the present disclosure.

What is claimed is:

1. A method for providing stimulation to tissue, comprising:
   introducing an arm and a wristed instrument, the wristed instrument positioned at a distal end of the arm and including a plurality of jaws, into a laparoscopic surgical site within a patient;
   accessing a stimulation probe with the wristed instrument, the stimulation probe including,
      a handle having a curved proximal end and a curved distal end, and
      a malleable needle axially-extending from the distal end and terminating at a conductive tip, the needle having a needle diameter between 0.5 and 1.5 millimeters,
   wherein the handle includes an axially-extending cylindrically elongate portion between the curved proximal end and curved distal end, the cylindrically elongate portion having an outer surface having a handle diameter greater than the needle diameter;
   wherein the handle and needle include an axial length that is less than 3.0 centimeters as measured from the proximal end of the handle to the conductive tip of the needle;
   introducing the stimulation probe into the laparoscopic surgical site such that the handle and the needle are within the patient;
   operating the arm and wristed instrument to grasp the handle of the stimulation probe with the plurality of jaws between a plurality of grooves on the handle, the plurality of grooves formed into the outer surface of the cylindrically elongate portion as circular grooves about an axis of the cylindrically elongate portion;
   moving the stimulation probe using the arm such that the conductive tip contacts a tissue site;
   bending the malleable needle to a desired shape with the arm; and
   delivering stimulation to the tissue site using the stimulation probe.

2. The method of claim 1, wherein the handle has a proximal end coupled to a flexible wire and the distal end is coupled to the needle, and wherein a length of the handle and the needle, as measured from the proximal end to the conductive tip, is less than 2.0 centimeters.

3. The method of claim 1, wherein the stimulation probe includes a first needle and a second needle coupled to the handle, the first needle delivering stimulation to the tissue site and the second needled sensing signals from the tissue site.

4. The method of claim 1, wherein the needle is covered in an insulating sheath extending from the handle to the conductive tip, wherein the conductive tip is characterized by an absence of the insulating material.

5. The method of claim 1, further comprising bending the needle to a desired shape and angle.

6. The method of claim 1 wherein the handle includes a distal section of the cylindrical elongate portion and a proximal section of the cylindrical elongate portion and wherein the plurality grooves include a first groove in the distal section and a second groove in the proximal section.

* * * * *